(12) United States Patent
Gallmann

(10) Patent No.: US 7,431,947 B2
(45) Date of Patent: Oct. 7, 2008

(54) HAIR TREATMENT COMPOSITIONS

(76) Inventor: Kuki Gallmann, Gigiri Road, P.O. Box 63704 00619, Nairobi, Kenya (KE)

( * ) Notice: Subject to any disclaimer, the term of this patent is extended or adjusted under 35 U.S.C. 154(b) by 0 days.

(21) Appl. No.: 11/282,088

(22) Filed: Nov. 17, 2005

(65) Prior Publication Data
US 2006/0198811 A1 Sep. 7, 2006

Related U.S. Application Data

(60) Provisional application No. 60/628,854, filed on Nov. 17, 2004.

(51) Int. Cl.
*A01N 65/00* (2006.01)
*A61K 36/00* (2006.01)
(52) U.S. Cl. .................. 424/725; 424/774; 424/779
(58) Field of Classification Search .................. None
See application file for complete search history.

(56) References Cited

U.S. PATENT DOCUMENTS 5,607,674 A * 3/1997 Rovesti et al. .............. 424/764

OTHER PUBLICATIONS

Beckley, V.A: East African Agr. J. (1936), 1, 469-70.*
Anonymous, "*Tarchonanthus camphoratus*", Agroforesttree Database URL: www.worldagroforestry.org.
Anonymous, Complete EO list, Internet Article URL: www.essentialoils.org.
Beentje, "The genus *Tarchonanthus* (Compositae-Mutisieae)", 1999 KEW Bulletin, vol. 54, No. 1, pp. 81-95.
Bishay et al. "Sesquiterpene Lactones and Flavanoid Glucoside with the Potent Biological Activities of *Tarchonanthus camphoratus* L", Bull. of Pharm. Sci. vol. 24, No. 2 2001.

* cited by examiner

*Primary Examiner*—Patricia Leith
*Assistant Examiner*—Qiuwen Mi
(74) *Attorney, Agent, or Firm*—Butzel Long

(57) ABSTRACT

A hair treatment composition that includes an aqueous formulation of leleshwa. The aqueous formulation of leleshwa is obtained by subjecting leleshwa to a steam distillation process to remove essential oils therefrom. The aqueous condensate phase from the steam distillation process is recovered and used as the aqueous formulation of leleshwa according to the present invention. The aqueous formulation of leleshwa is used alone as a rinse to treat hair or combined with other ingredients to form hair treatment compositions that include rinses, conditioners, shampoos and combinations thereof.

4 Claims, No Drawings

HAIR TREATMENT COMPOSITIONS

RELATED APPLICATION

The present application is based upon U.S. Provisional Patent Application Ser. No. 60/628,854 entitled "Hair Treatment Compositions" filed Nov. 17, 2004 to which priority is claimed under 35 U.S.C. §120, the entire specification of which is hereby expressly incorporated herein by reference.

TECHNICAL FIELD

The present invention relates to chemical compositions that are used to treat hair. More particularly, the present invention is directed to natural plant extracts that can be used alone or combined with other ingredients, and which improve the appearance and feel of hair.

BACKGROUND ART

Many different hair care products are used to treat hair. For example, shampoos are used to clear hair; conditioners are used to improve the texture of hair and styling gels are used to increase hair manageability. Not all hair care products, however, result in healthy hair. For example, some hair care products can remove natural components from hair causing damage. In addition, hair treatment processes such as dyeing, relaxing, or permanent waving can damage hair. Hair also can be damaged or weakened by the action of mechanical, atmospheric, and/or chemical exposure. For example, radicals from ultraviolet radiation and the peroxide treatment step of dying hair can cause damage that is evidenced by weakened, dry, and brittle hair. The most apparent effect is the bleached appearance of hair after exposure to intense sunlight during the summer months. Hair also can suffer abrasion damage caused by a multitude of factors such as grooming, combing, blow-drying, and curling.

The present invention is directed to natural plant extracts that have been found to improve the appearance and feel of hair.

DISCLOSURE OF THE INVENTION

According to various features, characteristics and embodiments of the present invention which will become apparent as the description thereof proceeds, the present invention provides a hair treatment composition that includes an aqueous formulation of leleshwa which is obtained from an aqueous condensate phase after essential oils are removed from leleshwa by a steam distillation process.

The present invention further provides a method of preparing a hair treatment formulation which involves:

subjecting at least one of leleshwa leaves, stems, branches, bark and roots to a steam distillation process in which essential oils are collected together with an aqueous phase;

separating the aqueous phase from the essential oils; and incorporating the aqueous phase into a hair treatment formulation.

The present invention further provides a method of treating hair which comprises applying a hair treatment composition that includes an aqueous formulation of leleshwa which is obtained from an aqueous condensate phase after essential oils are removed from leleshwa by a steam distillation process.

BEST MODE FOR CARRYING OUT THE INVENTION

The present invention is directed to natural plant extracts that can be used alone or combined with other ingredients as hair treatment compositions. In particular, the present invention involves an aqueous extract from *Tarchonanthus camphorates* which is a by-product of a steam distillation process that is used to extract oils from the leaves of *Tarchonanthus camphorate* plants.

The *Tarchonanthus camphoratus* is a shrub that is widespread in Southern Africa. It grows in thickets of bushveld, grassland, forests and semi-desert areas. It thrives in sandy soils and is abundant in the Rift uplands area. *Tarchonanthus camphorates* is a semi-deciduous small tree or shrub that grows in large uniform groups, but grows larger and more densely when it grows alone among other trees in the bush.

*Tarchonanthus camphorates* is known by a number of different names such as wild cotton, sage wood, African wild sage, wildesalie, kamferhout, kamferbos, sieriehout, vaalbos, veld-vaalbos, vaaibos, sauto mofahlana, rolog e thaalaping mohathla, well known in the local Maasai dialect with the name of "leleshua" or "leleshwa," (used herein) in the abissianian language "Ebok," the Swahili dialect "mikalambati, and so on.

The *Tarchonanthus camphoratus* has regular branches with velutinous white-greenish oval or lanceolate shaped leaves ranging from 4 to 13 cm length having a strong camphorated aromatic smell, whence its Linneana denomination.

Traditionally, leleshwa has many uses. The leaves are crushed and applied to the skin for cuts and wounds. Leleshwa is also used as a natural insect repellant by many tribes in Africa. The Massai often use the soft aromatic leaves of leleshwa as bedding, which is said to promote deep sleep and deter insects. In the western Cape region a hot poultice of the leaves is applied to the chest to relieve asthma, bronchitis and chest inflammations.

When crushed, leleshwa leaves emit a strong camphoraceous scent. Many wild animals that live in the areas where leleshwa grows, particularly cape buffaloes and black rhinos, have been observed rubbing themselves against a leleshwa tree or shrub. Upon closer inspection, it is revealed that those animals, which have crushed the leaves onto their skin, were relatively free from ticks.

U.S. Pat. No. 5,607,674 to Rovesti et al. discloses the use of *Tarchonanthus camphorate* or leleshwa and its derivatives in formulations and compositions having insect repellant, anti-irritant, anti-edema, decongestant and soothing properties. Rovesti et al. teaches the use of the essential oils from leleshwa which can be obtained from extraction methods including distillation.

The present invention is directed to the use of an aqueous formulation of leleshwa which is obtained as a by-product of a steam distillation process that is used to extract essential oils from the leaves of leleshwa. Although specific reference is made herein to a steam distillation process, it is to be understood that any extraction process that allows for the separation and collection of the water soluble components from the essential oils and starting materials, e.g. leaves, twigs, sticks, bark, roots, etc., can be used according to the present invention. Examples of other extraction processes include direct distillation in which leleshwa material is boiled in aqueous solution and the vapors are collected and condensed and indirect distillation in which leleshwa material is essentially steamed over a vat of boiling water and the vapors are collected and condensed. Other extraction processes that involve partial refluxing, solvent extraction to remove essential oils as a pre-treatment to water extraction/distillation, etc. can be used.

The boiling points of essential oils from plants are less than the boiling point of water. Moreover, essential oils have specific gravities that are more or less than the specific gravity of water. Accordingly, essential oils can be collected over (floating on) or under water.

Essential oils are held inside aromatic plant cells. Steam can be applied to disrupt the plant cells and release the essential oils.

In a steam distillation process to remove and collect essential oils from leleshwa, leaves are collected and placed in a container through which steam is passed. Typically in steam distillation processes steam is generated in a boiler and passed through a container which is configured to support materials in a manner which will expose the materials to the steam.

As the steam contacts the leaves, the plant cells are disrupted and the essential oils that have lower boiling points than the water (i.e., lower than the temperature of the steam that contacts the leaves) are releases and formed into vapors that are carried out of the container with the steam.

The mixture flow of essential oil and steam is directed to a condenser in which the mixture if cooled to form a liquid mixture, having an aqueous phase and an oil phase which separate according to the relative specific densities. According to the present invention the aqueous phase from the steam distillation of leleshwa is collected and used as a hair treatment formulation, or together with other ingredients.

During the course of the present invention it was unexpectedly discovered that when the aqueous formulation of the leleshwa which was normally discarded form the steam distillation process was used to rinse pets, i.e. dogs, the dogs' coats became very thick. Subsequent testing of the aqueous formulation of the leleshwa on humans using the aqueous formulation as a rinse resulted in improvements in the appearance and feel of hair as compared to merely rinsing with regular water. Observed improvements included hair thickness and body and definite signs of re-growth, and improvements in gloss and elasticity, with an overall attractive look of vigorous health. It was also noted that the aqueous formulation of the leleshwa used according to the present invention appeared to promote or stimulate hair growth as evidenced by the thickening of hair during human testing.

The aqueous formulation of the leleshwa recovered from the steam distillation process can be used as a hair treatment alone and either full strength or diluted or concentrated as desired. In addition, the aqueous formulation of the leleshwa can be combined together with other ingredients such as fats and fatty oils such as higher alcohols, liquid paraffin, glycerides, hydrocarbons and esters, nonionic surface-active agents, cationic surface-active agents, germicides, pigments, perfumes and the like which have been widely used in conventional hair rinse compositions. Other optional ingredients which are conventional in hair treatment formulations and useful in combination with the aqueous leleshwa formulation include additional conditioning agents, viscosity modifiers, suspending agents, preservatives, coloring agents, polyols such as glycerine and polypropylene glycol, chelating agents such as EDTA, antioxidants, fragrances, antimicrobials and sunscreens. In addition the aqueous formulation of the leleshwa can be combined together with other conventional ingredients to produce a shampoo formulation or a shampoo/conditioner formulation, or a hair treatment that is applied to hair as a spray, gel, cream or emulsion, a foam, etc, and combed, brushed or worked into the hair in any known manner, including thermo or heat-treatment.

In addition to the steam distillation process of leleshwa discussed above that involves the removal of essential oils from leleshwa leaves, it is also possible to conduct such stream distillation using roots, bark, stems and/or branches either fresh, dried or soaked and recover the aqueous formulation of the leleshwa used according to the present invention.

An analysis of an aqueous formulation of the leleshwa recovered from the steam distillation process if presented in Tables I and II below:

TABLE I

Volatile Organics (Capillary Column)
Tentatively Identified Compounds (TIC)

| CAS | Parameter | Result* | Units |
|---|---|---|---|
| 74-87-3 | Chloromethane | 11 | µg/L |
| 67-64-1 | 2-Propanone | 4500 | µg/L |
| 78-93-3 | 2-Butanone | 55 | µg/L |
| 78-83-1 | Isobutanol | 110 | µg/L |
| 108-88-3 | Toluene | 5.1 | µg/L |
| 1606-47-9 | 4-methyl-1-penten-3-one | 5800 | µg/L |
| 66-25-1 | Hexanal | 1100 | µg/L |
| 507-70-0 | Borneol | 3100 | µg/L |

Instrument: GC/MS VOA
Prep: purge and trap method for organic analytes
*Estimated concentrations, TIC by GC/MS. Compounds listed in order of retention time.

TABLE II

Semi-Volatile Organics (Base/Neutral/Acid Fractions)
Tentatively Identified Compounds (TIC)

| CAS | Parameter | Result* | Units |
|---|---|---|---|
| 470-82-6 | Eucalyptol | 82,000 | µg/L |
| 4695-62-9 | 1,3,3-Trimethyl-bicyclo[2,2,1]heptane-2-ol | 100,000 | µg/L |
| 020126-76-5 | 3-Cyclohexen-1-ol,4-methyl-1-(1-methylethyl)-,(R)- | 100,000 | µg/L |
| 6728-26-3 | 2-hexenal | 2500 | µg/L |
| 544-12-7 | 3-hexen-1-ol | 3300 | µg/L |
| 79-92-5 | Camphene | 32000 | µg/L |
| 515-00-4 | 6,6-dimethyl-bicyclo[3,1,1]hept-2-ene-2- | 2000 | µg/L |

Instrument: GC/MS SVOA
*Estimated concentrations, TIC by GC/MS. Compounds listed in order of retention time.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above and recited in the attached claims.

What is claimed is:

1. A hair treatment composition comprising an extract of *Tarchonanthus camphorates* (leleshwa), wherein said extract is obtained by subjecting leleshwa to steam distillation or water distillation to remove essential oils and collecting the aqueous condensate of the steam distillation or water distillation, and wherein said composition further comprises at least one agent selected from the group consisting of a viscosity modifier, a paraffin, a suspending agent, a preservative, a pigment, a coloring agent, a polyol, a chelating agent, an antioxidant, a fragrance, an antimicrobial, a germicide and a sunscreen agent.

2. The hair treatment composition according to claim 1, in the form of one of a liquid, a gel, a cream or a foam.

3. The hair treatment composition according to claim 1, wherein said composition is a hair conditioner, a hair shampoo, or a hair shampoo and hair conditioner.

4. The hair treatment composition according to claim 1, wherein the extract of leleshwa is obtained from a part of leleshwa selected from the group consisting of leaves, stems, branches, bark and roots.

\* \* \* \* \*